US009957286B2

United States Patent
Galindo Esquivel et al.

(10) Patent No.: US 9,957,286 B2
(45) Date of Patent: May 1, 2018

(54) METHOD FOR THE SYNTHESIS OF SOLID HETEROGENEOUS CHIRAL CATALYSTS AND THEIR USE IN STEREOSELECTIVE REACTIONS

(71) Applicant: Universidad de Guanajuato, Guanajuato (MX)

(72) Inventors: Ignacio Rene Galindo Esquivel, Guanajuato (MX); Juan Manuel Juarez Ruiz, Guanajuato (MX); Orlando Regalado Oliva, Guanajuato (MX)

(73) Assignee: Universidad de Guanajuato, Guanajuato (MX)

( * ) Notice: Subject to any disclaimer, the term of this patent is extended or adjusted under 35 U.S.C. 154(b) by 0 days. days.

(21) Appl. No.: 15/427,179

(22) Filed: Feb. 8, 2017

(65) Prior Publication Data

US 2017/0145041 A1    May 25, 2017

Related U.S. Application Data

(62) Division of application No. 14/085,003, filed on Nov. 20, 2013, now Pat. No. 9,598,348.

(30) Foreign Application Priority Data

Nov. 20, 2012  (MX) .................... MX/a/2012/013420

(51) Int. Cl.
| | | |
|---|---|---|
| C07C 201/12 | (2006.01) |
| C07F 7/18 | (2006.01) |
| B01J 31/06 | (2006.01) |
| C07D 209/34 | (2006.01) |

(52) U.S. Cl.
CPC ............ *C07F 7/1836* (2013.01); *B01J 31/062* (2013.01); *B01J 31/069* (2013.01); *C07C 201/12* (2013.01); *C07D 209/34* (2013.01); *B01J 31/061* (2013.01); *B01J 2231/342* (2013.01); *B01J 2231/346* (2013.01); *B01J 2231/348* (2013.01)

(58) Field of Classification Search
CPC .................................................. C07C 201/12
See application file for complete search history.

(56) References Cited

U.S. PATENT DOCUMENTS

| | | |
|---|---|---|
| 5,990,318 A | 11/1999 | Chan et al. |
| 6,028,025 A | 2/2000 | Ying et al. |
| 7,291,739 B2 | 11/2007 | Spivey et al. |
| 7,541,456 B2 | 6/2009 | MacMillan et al. |
| 8,084,641 B2 | 12/2011 | Wang |
| 8,148,287 B2 | 4/2012 | Ying et al. |

FOREIGN PATENT DOCUMENTS

| | | |
|---|---|---|
| EP | 1479439 A1 | 11/2004 |
| ES | 2349604 A1 | 1/2011 |

OTHER PUBLICATIONS

Office Action dated May 19, 2016 in U.S. Appl. No. 14/085,003, by Galindo Esquivel.
Search Report dated Mar. 14, 2016 in MX Application No. MX/a/2012/013420.
Search Report dated Jan. 31, 2014 in EP Application No. 13193738.5.

*Primary Examiner* — Shawquia Jackson
(74) *Attorney, Agent, or Firm* — Panitch Schwarze Belisario & Nadel LLP

(57) ABSTRACT

This invention describes the methodology to produce solid heterogeneous chiral organocatalysts that can be used in condensation reactions. The catalysts can be recovered in a simple manner by filtration and can also be reused.

16 Claims, No Drawings

METHOD FOR THE SYNTHESIS OF SOLID HETEROGENEOUS CHIRAL CATALYSTS AND THEIR USE IN STEREOSELECTIVE REACTIONS

CROSS-REFERENCE TO RELATED APPLICATIONS

This application is a Divisional of U.S. patent application Ser. No. 14/085,003 filed Nov. 20, 2013, now U.S. Pat. No. 9,598,348, issued Mar. 21, 2017 and the disclosure of which is incorporated herein by reference.

FIELD OF THE INVENTION

This invention describes a method for the synthesis of solid heterogeneous chiral catalysts and their use in stereoselective reactions. Particularly, the invention describes a methodology for obtaining organic catalysts immobilized in a silicon oxide matrix. These catalysts are applied in some stereoselective reactions; they are easily recovered from the reaction mixture and are reused.

BACKGROUND OF THE INVENTION

There is a set of molecules known as chiral molecules which have identical chemical formulas, but have a different spatial distribution. These molecules have very similar physical and chemical properties, which makes it difficult to separate them using conventional methods used in the chemical industry (crystallization, adsorption, etc.). On the other hand, unlike the physical and chemical properties, the biological properties of these molecules can be extremely different, e.g., a molecule with a three-dimensional arrangement can affect a living organism, while another one with the inverse arrangement can act as medication. This type of phenomena is common and widely known in the chemistry of enzymes. The chemistry of nature is stereoselective, i.e., it favors the formation of only one of the two three-dimensional arrangements that the chiral molecules can have. Each compound with a determined three-dimensional arrangement is called an "enantiomer".

A large quantity of medications available in the market use chiral molecules as active ingredients. Since 1992, the FDA prohibited the use of racemic mixtures (50/50 mixture of enantiomers) when one of the enantiomers has an unknown or adverse pharmacological activity. Currently, the pharmaceutical industry directs its efforts to offering enantiomerically pure medications. However, to date, there are still medications sold as racemic mixtures. When it is confirmed that any of the enantiomers has adverse effects to the organism it is obligatory to separate the mixture of enantiomers until only the desired active enantiomer is obtained.

As previously mentioned, enantiomers have very similar physical and chemical properties which makes it difficult to separate them. The preferred procedure for the production of pharmaceuticals involves the synthesis of racemic mixtures using non-selective catalysts, and once the racemic mixture is obtained, a series of separations is done by means of diastereomeric resolution until the desired purity of the active enantiomer is achieved. In order to achieve the separation, an enantiomerically pure compound (generally obtained from a natural source) is used, which is made to react with the racemic compound so as to obtain a mixture of diastereomers. Unlike enantiomers, diastereomers have different physical properties, which allows their separation (generally through crystallization). Once separated, the inverse reaction for forming the diastereomers is carried out in order to obtain the desired enantiomer and recover the auxiliary chiral compound used in the separation, which can be recycled. This process generates low yields and useless byproducts.

An alternative process has been proposed which postulates using a stereoselective catalyst during the synthesis of the chiral compound; this favors the formation of one enantiomer, reducing or preventing the need for purification processes after the reaction.

Since approximately a decade ago, stereoselective compounds have been actively sought out. The chiral catalysts most investigated involve "organometallic" molecules which include in their formation precious metals such as Pt, Pd, Rh, etc. Generally, these types of catalysts are sensitive to oxidizing atmospheres, which causes greater difficulty in handling during their synthesis and in their use to catalyze the production of chiral molecules. Moreover, these catalysts are homogeneous, so it is necessary to carry out a separation of the catalyst and the reaction mixture, downstream. In order to avoid this final difficulty, it has been proposed to bind organometallic catalysts to various substrates (U.S. Pat. No. 6,028,025 and U.S. Pat. No. 5,990,318).

As an alternative to the organometallic catalysts, there are the so-called "organocatalysts." These are organic chiral molecules that do not contain metals within their formation (U.S. Pat. No. 8,084,641, U.S. Pat. No. 7,541,456, and U.S. Pat. No. 7,291,739). One of its main advantages is that they are not sensitive to oxidizing atmospheres, however, because they are less active than organometallic catalysts, they require greater reaction times. These catalysts are also homogeneous. However, to date, few efforts have been made to immobilize these type of systems in solid matrices (U.S. Pat. No. 8,148,287; K. Sakthivel, W. Notz, T. Bui, C. F. Barbas III, *J. Am. Chem. Soc.* 123, 5260-5267, 2001; F. Calderón, R. Fernández, F. Sánchez, A. Fernández-Mayoralas, *Adv. Synth. Catal.* 347, 1395-1403, 2005; and E. G. Doyagüez, F. Calderón, F. Sánchez, A. Fernández-Mayoralas, *J. Org. Chem.* 72, 9353-9356, 2007). In U.S. Pat. No. 8,148,287, the anchor of organic catalysts is reported in a silicone foam using 1,2,3-triazole as linker between the inorganic and the organic part. F. Calderón et al. and E. G. Doyagüez et al. are developing a method for the synthesis of heterogeneous chiral catalysts using 4-hydroxyproline as organic catalyst, which is anchored to previously synthesized oxide supports MCM-41, silica, ITQ2 and ITQ6. The amino acid is anchored to the solid matrix through the hydroxyl group.

In a similar manner, K. Sakthivel et al. uses a method of proline immobilization in a silica gel support. However, the amino acid is not covalently bonded to the support. There is a recent report in which proline anchored to mesostructured catalysts (MCM-41) was synthesized in just one step; however, this synthesis process involves the use of colloidal silica previously synthesized as a substrate for the anchoring (E. A. Prasetyanto, S. C. Lee, S. M. Jeong, S. E. Park, *Chem. Commun.* 1995-1997, 2008). In this procedure, the amino acid is anchored to the MCM-41 in the carboxyl group of the proline. In general, the processes used to immobilize the organic catalysts involve the anchoring of the organic catalyst by means of the formation of covalent bonds with a previously synthesized oxide surface, which allows the maximum anchoring of approximately 10% in weight of the organic catalyst.

Very recently, García-Doyagüez et al. in 2009, described in Spanish Patent No. 2349604 the construction of an organic polymer of hydroxyproline and its use as catalyst. The invention uses organic polymers based on vinyl monomers, and reports activity in aldol condensation with minimum reaction times of 24 hours and 97% conversion, obtaining enantiomeric selectivity with 1:1 proportion for the most active catalyst.

The reported reaction times to achieve conversions greater than 80% during aldol condensation reactions vary from 24 to 72 hours when homogeneous organic catalysts are used (K. Sakthivel, W. Notz, T. Bui, C. F. Barbas III, *J. Am. Chem. Soc.* 123, 5260-5267, 2001), of approximately 24 to 48 hours for heterogeneous catalysts, obtained by traditional anchoring methods available in the literature (F. Calderón, R. Fernández, F. Sánchez, A. Fernández-Mayoralas, *Adv. Synth. Catal.* 347, 1395-1403, 2005; E. G. Doyagüez, F. Calderón, F. Sánchez, A. Fernández-Mayoralas, *J. Org. Chem.* 72, 9353-9356, 2007), while the visible reaction time when using the catalysts obtained through the methodology described in this invention varies from 2 to 6 hours.

This invention reports a new and innovative methodology in the synthesis of heterogeneous chiral catalysts, and generates the silicone oxide solid matrix using functionalized monomer with the organic catalyst properly protected, which allows obtaining solid heterogeneous chiral catalysts with approximately 30% in weight of the organic catalyst. The synthesis process includes four stages of reaction that are low cost and simple to develop, with high yield, and that do not use sophisticated purification processes. Only in stages 3 and 4 is the solid product purified by simple washing with organic or aqueous solvent. Furthermore, the catalysts obtained in this invention catalyze condensation reactions in a stereoselective manner.

BRIEF SUMMARY OF THE INVENTION

This invention relates to the development of a method for obtaining solid heterogeneous chiral catalysts comprising an organic part comprising an α-amino acid, and an inorganic part consisting of a silicon oxide matrix; as well as its application in reactions for forming stereoselective carbon-carbon bonds. The methodology for the synthesis of the catalyst can be utilized for α-amino acids such as: valine, proline, alanine, phenylglycine, phenylalanine, leucine, isoleucine, or methionine.

A method for the synthesis of solid heterogeneous chiral catalysts in which the method consists of the following 4 reaction stages described below:

Stage I Protection reaction of the amino group of the α-amino acid.

The first stage consists of a protection reaction of the amino group of the α-amino acid with tert-butyloxycarbonyl (Boc).

0.5 to 3.0 equivalents of di-tert-butyl carbonate ($BOC_2O$) are added to a solution of 0.1 to 2.0M of α-amino acid in a mixture of distilled water, and 1,4-dioxane (with a proportion of 1:0.5 to 1:2 in volume) at a temperature from 0° C. to 30° C. 0.3 to 3.0 equivalents of triethylamine (TEA) are added to the reaction mixture. The reaction mixture is kept continuously stirring at a temperature from 20° C. to 40° C. for 12 to 72 hours. The reaction mixture is partially concentrated and the solution is extracted with ethyl acetate. The organic phase is separated and dried with sodium sulphate or anhydrous magnesium sulphate. The solution is concentrated in order to obtain the crude product.

Stage II Silanization reaction between the α-amino acid protected with tertbutyloxycarbonyl (Boc) (the product from Stage I) and aminopropyltriethoxysilane (APTES). 0.5 to 3.0 equivalents of potassium carbonate ($K_2CO_3$) and from 0.5 to 3.0 equivalents of O-(benzotriazol-1-yl)-N,N,N',N'-tetramethyluronium-tetrafluoroborate (TBTU) are added to a 0.1 to 0.2M solution of the α-amino acid protected with Boc in acetonitrile ($CH_3CN$) or methanol ($CH_3OH$) while stirring at a temperature from 0° C. to 40° C. under a nitrogen atmosphere. The reaction mixture is kept stirring for 10 to 60 minutes. 0.5 to 5.0 equivalents of APTES are added to the reaction mixture. The reaction mixture is kept at a temperature from 20° C. to 40° C. for 12 to 72 hours. The reaction mixture is filtered and the filtrate is washed with acetonitrile or methanol. The filtrate is concentrated with a vacuum in order to obtain the crude product, which corresponds to the α-amino acid protected with Boc and bonded by the carboxyl group to the amino group of the APTES.

Stage III Inorganic polymerization reaction of the Stage II crude product.

1.0 to 20 equivalents of silicon alkoxide are added to a 0.1 to 2.0M solution of the crude compound obtained in Stage II in ethanol ($CH_3CH_2OH$) or methanol. Furthermore, 0.1 to 3.0 equivalents of a basic catalyst (such as potassium carbonate) or of an acid catalyst (such as acetic acid ($CH_3CO_2H$) can be added to this mixture. The reaction mixture is heated to 40 to 80° C. for 0.1 to 12 hours. 30 to 100 equivalents of distilled water are slowly added to the reaction mixture at a temperature from 40 to 80° C. The reaction mixture is continuously stirred at a temperature from 40 to 80° C. for 0.5 to 24 hours (until a gel is formed). The reaction mixture is left to stand at a temperature from 20 to 30° C. while ventilated for 24 to 72 hours. The gel is dried at 40 to 90° C. for 24 to 72 hours. The solid is pulverized and washed with methanol and dichloromethane ($CH_2Cl_2$) in order to obtain the solid heterogeneous chiral catalyst protected with Boc.

Stage IV Deprotection reaction, or activation of the solid heterogeneous chiral catalyst obtained in Stage III.

Trifluoroacetic acid ($CF_3CO_2H$) or 3M hydrochloric acid in ethyl acetate (HCl/EtOAc) in mass/volume (g/mL) proportion of 1/0.1 to 1/5 is added to a suspension of the Stage III product (or Stage IV) in dichloromethane, chloroform ($CHCl_3$) or dichloroethane ($ClCH_2CH_2Cl$) in mass/volume (g/mL) proportion of 1/10. The reaction mixture is stirred at a temperature from 0 to 25° C. for 3 to 72 hours. The reaction mixture is decanted and the solid is neutralized with an aqueous solution of $Na_2CO_3$ or $NaHCO_3$ at 10 to 20%. The activated solid heterogeneous chiral catalyst is filtered and washed with distilled water. The catalyst is dried at 40 to 80° C. for 10 to 72 hours.

For the method described in this invention to work, it is necessary to carry out each and every one of the Stages I, II, III and IV described herein. Nevertheless, the fundamental stage of the method is indicated in Stage III, which is the inorganic polymerization of the silicon alkoxide with the α-amino acid protected with Boc product of Stage II. Alternatively, a method for the synthesis of heterogeneous chiral catalysts can be used in which the α-amino acid protected with Boc (product of Stage II) is covalently bonded with the amino group of a silicon oxide solid matrix, as described below:

Stage V Inorganic polymerization of APTES.

From 0.1 to 3.0 equivalents of potassium carbonate and from 1.0 to 20 equivalents of silicon alkoxide are added to a solution of 0.1 to 2.0M of APTES in ethanol or methanol.

The reaction mixture is heated at a temperature from 40 to 80° C. for 0.1 to 12 hours. 30 to 100 equivalents of distilled water are slowly added to the reaction mixture at a temperature from 40 to 80° C. The reaction mixture is constantly stirred at a temperature from 40 to 80° C. until a gel is formed. The mixture reaction is left to stand at a temperature from 20 to 30° C. while vented for 24 to 72 hours. The gel is dried at a temperature from 40° C. to 90° C. for 24 to 72 hours. The solid is pulverized in order to obtain a silicon oxide powder highly substituted with amino groups on the surface.

Stage VI Reaction of the solid matrix (product of Stage V) with the α-amino acid protected with Boc (product of Stage I).

From 0.5 to 3.0 equivalents of K₂CO₃ and from 0.5 to 3.0 equivalents of TBTU are added to a solution of 0.1 to 1.5M of the α-amino acid protected with Boc in acetonitrile or methanol while stirring at 0° C. to 40° C. under a nitrogen atmosphere. The reaction mixture is stirred for 10 to 60 minutes. The solid obtained in Stage V in a mass/volume (g/mL) proportion of 1/5 to 1/30 is added to the reaction mixture. The reaction mixture is kept at a temperature from 20° C. to 40° C. for 12 to 72 hours. The suspension is filtered and the filtrate is washed with acetonitrile or methanol. The filtrate is dried in a vacuum in order to obtain the crude product.

The deprotection, or activation reaction, of the heterogeneous chiral catalyst obtained in Stage VI is performed as described in Stage IV.

DETAILED DESCRIPTION OF THE INVENTION

The solid heterogeneous chiral catalyst obtained by any of these methodologies can be used in reactions for forming carbon-carbon bonds of a chiral nature, such as aldol condensation, Mannich condensation, Michael addition and Henry reaction using aqueous reaction mediums or organic mediums. The reactions can be done at temperatures from −78° C. to 40° C.

EXAMPLES

Example 1

Synthesis of a solid heterogeneous chiral catalyst based on L-proline.

Stage I

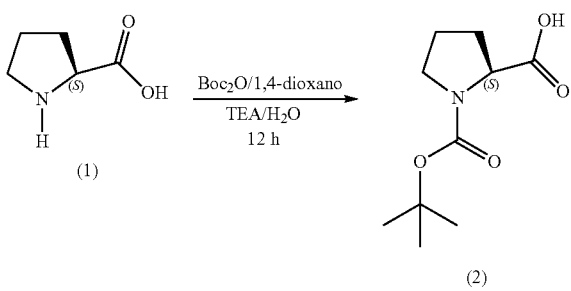

Protection Reaction with Boc of the Amino Group of L-Proline (1)

1.1 equivalents of BOC₂O were added to a 0.5M solution of L-proline (1) in a mixture of distilled water and 1,4-dioxane (1:1) at a temperature of 0° C. Once the mixture was homogenized, 1.1 equivalents of TEA were slowly added. The reaction mixture was continuously stirred for 12 hours at 25° C. The reaction mixture was partially concentrated, and the solution extracted with ethyl acetate. The organic phase was separated and dried with anhydrous sodium sulphate. The solution was concentrated in order to obtain N-Boc L-proline (2) in 98% yield. The product was not purified and was subjected to the following reaction as crude.

Stage II

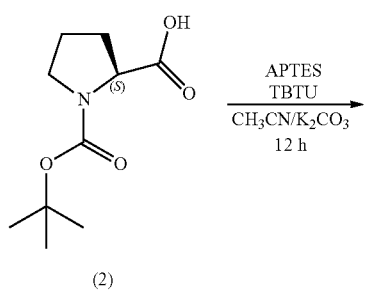

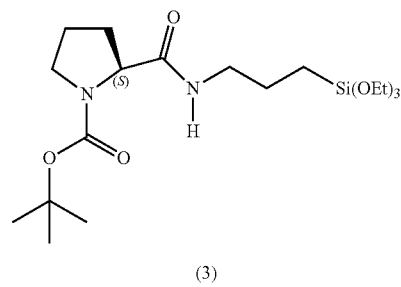

Silanization Reaction of the Compound (2) with APTES 1.0 equivalent of potassium carbonate and 1.5 equivalents of TBTU were added to a 0.2M solution of the compound (2) in acetonitrile at 0° C. while subjected to a nitrogen atmosphere. The mixture was continuously stirred for 60 minutes and 1.0 equivalent of APTES was later added. The reaction mixture was kept at 25° C. for 12 hours. The reaction mixture was concentrated, and to the resulting viscous product ethyl acetate was added and the suspension filtered. The resulting solution was concentrated, producing a lightly-yellow viscous liquid (3).

Stage III

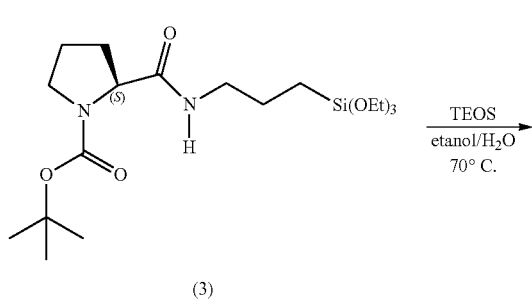

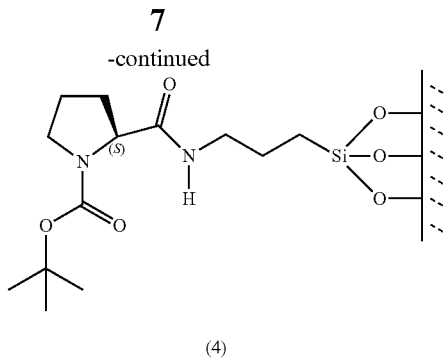

(4)

Polymerization Reaction of the Compound (3)

0.5 equivalent of potassium carbonate and 3.0 equivalents of tetraethyl orthosilicate (TEOS) were added to a 0.3M solution of the compound (3) in ethanol. The reaction mixture was heated at 70° C. for 2 hours. 30 equivalents of distilled water were slowly added to the reaction mixture at 70° C. The reaction mixture was continuously stirred at 70° C. until a gel was formed. The reaction mixture was left to stand at 25° C. while vented for 24 to 72 hours. The gel was dried at 60° C. for 48 hours. The solid was pulverized and the powder washed with methanol and dichloromethane in order to obtain a yellowish powder corresponding to compound (4).

Stage IV

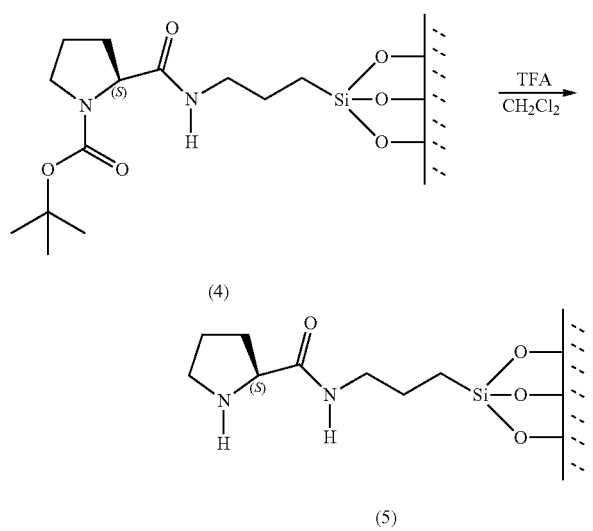

Deprotection or Activation Reaction of the Compound (4)

0.1 mL of trifluoroacetic acid was added to a suspension of the compound (4) in dichloromethane using 1 g of solid per 10 mL of solvent. The reaction mixture was kept at 0° C. and stirred for 3 hours. The reaction mixture was decanted and the solid neutralized with an aqueous solution of $NaHCO_3$ at 10%. The activated heterogeneous chiral catalyst was filtered and washed with distilled water. The catalyst was dried at 80° C. for 48 hours obtaining a fine powder with a slightly yellowish coloring. If preferred, the catalyst (5) can be used in aqueous reactions without previously drying.

The solid heterogeneous chiral catalyst or compound (5) was characterized by nuclear magnetic resonance of $^{13}C$ in the solid state, and the signals corresponding to the expected catalyst were observed: $^{13}C$ cross polarization magic angle spinning (CP-MAS) NMR (16 kHz, $CDCl_3$) ppm: δ=9.7 (CA), 24 (CB), 30.7 (CC), 41.1 (CD), 46.5 (CE), 60.9 (CF), 174.8 (CG). The elemental analysis indicates the presence of 31.5% by weight of the organic catalyst in the heterogeneous chiral catalyst.

Example 2

Synthesis of a Solid Catalyst Based on L-Proline

Stage I was carried out as described in Example 1 in order to obtain N-Boc L-proline (2). Later, the esterification of N-Boc L-proline (2) with 9-bromononanol was done in order to obtain the compound (6). The reaction proceeds as follows:

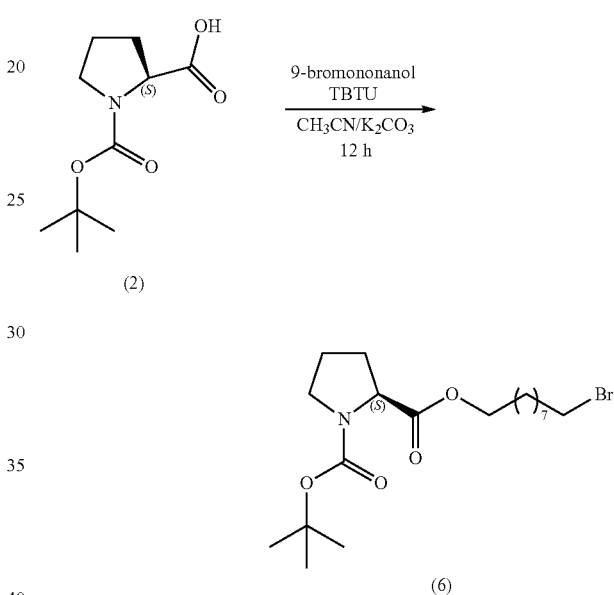

Esterification of N-Boc L-propline 1.0 equivalent of potassium carbonate and 1.5 equivalents of TBTU were added to a 0.2M solution of N-Boc L-proline (2) in acetonitrile at 0° C. under a nitrogen atmosphere. The reaction mixture was stirred for 60 minutes. 1.0 equivalent of 9-bromononanol is added to the reaction mixture. The reaction mixture was stirred for 12 hours. The reaction mixture was concentrated and the product was purified by column chromatography using silica gel as the immobile phase and a mixture of hexanes/ethyl acetate (3/1) as mobile phase in order to obtain the compound (6) in 92% yield.

The compound (6) was subjected to Stage II:

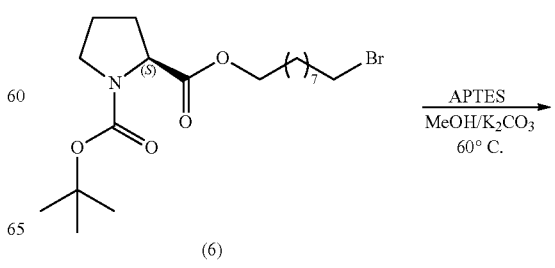

-continued

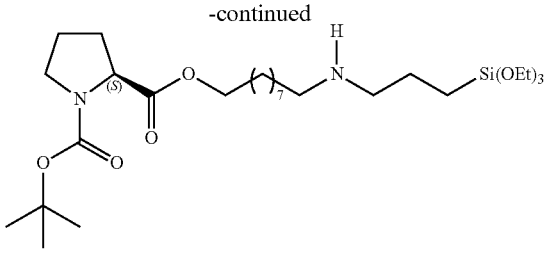

(7)

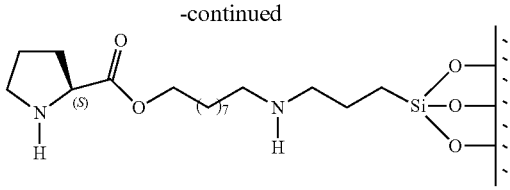

(9)

Silanization Reaction of the Compound (6) with APTES 1.0 equivalent of potassium carbonate and 1.0 equivalent of APTES are added to a 0.2M solution of the compound (6) in methanol at ambient temperature under a nitrogen atmosphere. The reaction mixture, while being stirred, was heated to 60° C. for 12 hours. The reaction mixture was concentrated and the unpurified compound (8) was used in the following reaction. Compound (7) was subjected to Stage III of inorganic polymerization as in Example 1, but 6.0 equivalents of TEOS were used.

Compound (7) was subjected to Stage III:

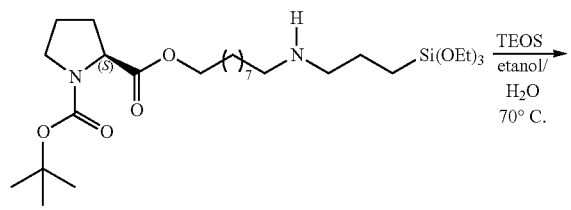

(7)

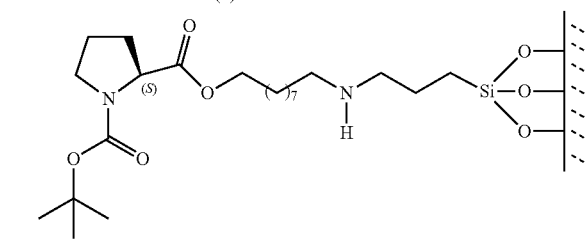

(8)

Polymerization Reaction of Compound (7)

0.5 equivalents of potassium carbonate and 6.0 equivalents of TEOS were added to a 0.3M solution of compound (7) in ethanol. The reaction mixture was heated to 70° C. for 2 hours. 30 equivalents of distilled water were slowly added to the reaction mixture at 70° C. The reaction mixture was continuously stirred at 70° C. until a gel was formed. The reaction mixture was left to stand at 25° C. while vented for 24 to 72 hours. The gel was dried at 60° C. for 48 hours. The solid was pulverized and the powder was washed with methanol and dichloromethane in order to obtain a yellowish powder corresponding to compound (8).

Compound (8) is subjected to Stage IV.

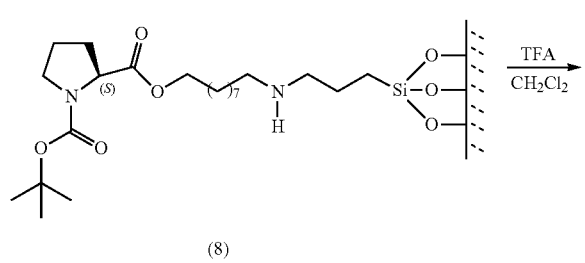

(8)

Deprotection or Activation Reaction of the Compound (8)

0.1 mL of trifluoroacetic acid was added to a suspension of the compound (8) in dichloromethane using 1.0 g of solid per 10 mL of solvent. The reaction mixture was stirred at 0° C. for 3 hours. The reaction mixture was decanted and the solid was neutralized with an aqueous solution of $NaHCO_3$ at 10%. The activated heterogeneous chiral catalyst was filtered and washed with distilled water. The catalyst was dried at 80° C. for 48 hours, producing a fine powder with a slightly yellowish coloring. If preferred, the catalyst (9) can be used in aqueous reactions without previous drying.

The catalyst (9) was characterized by nuclear magnetic resonance of $C^{13}$, in which the signals corresponding to the expected catalyst were observed: $^{13}C$ CP MAS NMR (16 kHz, $CDCl_3$) ppm: δ=9.8 (Ca), 20.5 (Cb), 28.7 (Cc), 43.9 (Cd), 49.1 (Ce), 51.8 (Cf), 59.7 (Cg), 67.5 (Ch), 162 (Ci). The elemental analysis indicated the presence of 21% by weight of the organic catalyst in the final solid.

This example shows that Stages I, II, III and IV described in this invention are always present to carry out the synthesis of solid catalysts with modified α-amino acids, although modification of the α-amino acids implies additional reaction steps. In order to obtain the solid heterogeneous chiral catalyst, it is necessary to include each and every one of the Stages I, II, III and IV or alternatively Stages I, V, VI and IV described in the methodology of the invention.

Example 3

Use of catalyst (5) in the aldol condensation of 4-nitrobenzaldehyde with acetone.

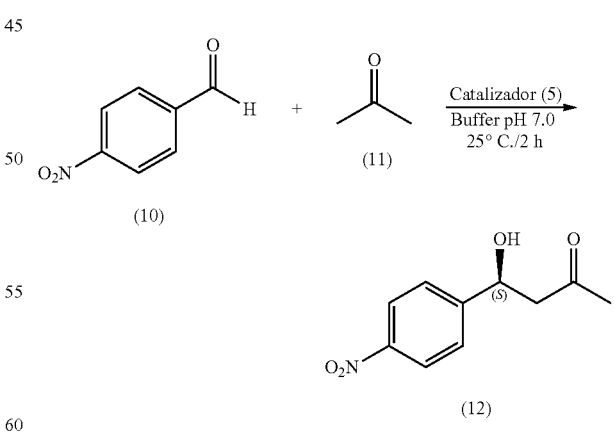

Aldol Condensation Catalyzed with Catalyst (5)

Acetone (11, 3.305 mmol) and 0.1 g of catalyst (5) were added to a 0.3M solution of 4-nitrobenzaldehyde (10, 0.661 mmol) in a phosphate buffer pH=7 (0.05M) at 25° C. The reaction mixture was kept stirring at 25° C. for 2 hours. The suspension was filtered, and the solution was partially concentrated and extracted with ethyl acetate. The organic phase was dried with anhydrous sodium sulfate and concentrated with a vacuum. The product was purified by column chromatography n order to obtain the β-hydroxyketone compound (12) in 98% yield with an enantiomeric excess of 79% corresponding to the (S)-enantiomer.

Example 4

Use of catalyst (5) in the aldol condensation reaction of 3-nitrobenzaldehyde with acetone.

This reaction with 3-nitrobenzaldehyde used the same reaction conditions used in Example 3 in 3 hours. The corresponding β-hydroxyketone product was obtained in 92% yield and in 64% enantiomeric excess of the (S)-enantiomer.

Example 5

Use of catalyst (5) in the reaction of aldol condensation of isatin with acetone.

This reaction with isatin used the same reaction conditions used in Example 3 in 3 hours. The corresponding β-hydroxyketone product was obtained in 76% yield and 84% enantiomeric excess of the (R)-enantiomer.

Example 6

Use of catalyst (9) in the aldol condensation reaction of 4-nitrobenzaldehyde with acetone.

This reaction with catalyst (9) used the same reaction conditions used in Example 3 in 4 hours. The corresponding β-hydroxyketone product was obtained in 75% yield and in 69% enantiomeric excess of the (S)-enantiomer.

Example 7

Use of catalyst (9) in the aldol condensation reaction of 3-nitrobenzaldehyde with acetone.

This reaction with catalyst (9) and 3-nitrobenzaldehyde used the same reaction conditions used in Example 3 in 4 hours. The corresponding β-hydroxyketone product was obtained in 67% yield and in 55% enantiomeric excess of the (S)-enantiomer.

Example 8

Use of catalyst (9) in the aldol condensation reaction of isatin with acetone.

This reaction with catalyst (9) and isatin used the same reaction conditions used in Example 3 in 6 hours. The corresponding β-hydroxyketone product was obtained in 58% yield and 76% enantiomeric excess of the (R)-enantiomer.

Example 9

Reusing catalyst (5) in the aldol condensation reaction of 4-nitrobenzaldehyde with acetone.

The aldol condensation reaction of 4-nitrobenzaldehyde with acetone was done using catalyst (5) as described in Example 3. The catalyst (5) was filtered, washed with acetone, and added to a new 0.3M solution of 4-nitrobenzaldehyde (0.661 mmol) in a phosphate buffer pH=7 (0.05M) at 25° C. with acetone (3.305 mmol). This reusing process was repeated for several cycles, obtaining the results shown in Table 1.

TABLE 1

Reusing of catalyst (5) with 4-nitrobenzaldehyde and acetone

| 4-nitrobenzaldehyde Reuse | Results Yield | Time | Enantiomeric excess (%) |
|---|---|---|---|
| 0 | 98% | 2 h | 79 (S)-(−) |
| 1 | 96% | 2 h | 79 (S)-(−) |
| 2 | 92% | >2 h | 79 (S)-(−) |
| 3 | 82% | >2 h | 76 (S)-(−) |
| 4 | 80% | ≈3 h | 69 (S)-(−) |

Example 10

Reusing catalyst (9) in the aldol condensation reaction of 4-nitrobenzaldehyde with acetone.

The aldol condensation reaction of 4-nitrobenzaldehyde with acetone was done using catalyst (9) as described in Example 3. The catalyst (9) was filtered, washed with acetone, and added to a new solution of 0.3M of 4-nitrobenzaldehyde (0.661 mmol) in a phosphate buffer (0.05M) at 25° C. with acetone (3.305 mmol). This reusing process was repeated for several cycles, obtaining the results shown in Table 2.

TABLE 2

Reusing of catalyst (9) with 4-nitrobenzaldehyde and acetone

| 4-nitrobenzaldehyde Reuse | Results Yield | Time | Enantiomeric excess (%) |
|---|---|---|---|
| 0 | 75% | 4 h | 69 (S)-(−) |
| 1 | 70% | 4 h | 66 (S)-(−) |
| 2 | 70% | 5 h | 63 (S)-(−) |
| 3 | 66% | 6 h | 59 (S)-(−) |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

Having described my invention sufficiently, I claim as my property what is contained in the following claims.

We claim:

1. A compound of formula (I):

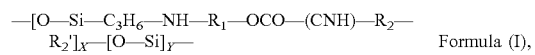

wherein $R_1$ is an aliphatic chain of the formula —$(CH_2)_n$—; n represents an integer of 0 to 9;

X and Y have a proportion of 1:1 to 1:20; and —OCO—(CNH)—$R_2$—$R_2$' represents an α-amino acid selected from the group consisting of proline

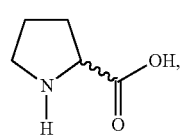

valine

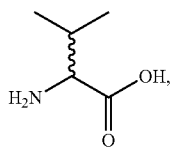

alanine

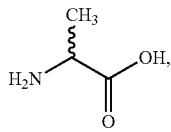

phenylglycine

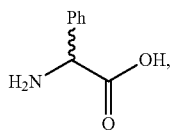

phenylalanine

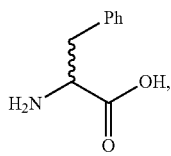

leucine

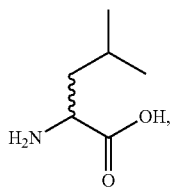

isoleucine

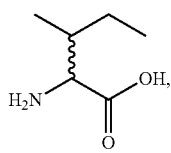

and methionine

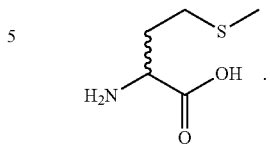

2. The compound of formula (I) according to claim 1, wherein n is 0 and the α-amino acid is proline.

3. The compound of formula (I) according to claim 1, wherein n is 9 and the α-amino acid is proline.

4. The compound of formula (I) according to claim 2, wherein X is 1 and Y is 3.

5. The compound of formula (I) according to claim 3, wherein X is 1 and Y is 6.

6. A method for forming chiral carbon-carbon bonds comprising performing a reaction for forming carbon-carbon bonds in the presence of the compound of formula (I) according to claim 1 as a catalyst, wherein the reaction for forming carbon-carbon bonds is selected from the group consisting of an aldol condensation, a Michael addition, a Mannich reaction, and a Henry reaction.

7. The method according to claim 6, wherein the reaction for forming carbon-carbon bonds is performed in an aqueous reaction medium or an organic reaction medium at a temperature of −78° C. to 40° C.

8. The method according to claim 6, wherein the reaction for forming carbon-carbon bonds is performed in an aqueous reaction medium comprising a phosphate buffer having pH 7 at a temperature between 0° C. and 10° C.

9. The method according to claim 6, wherein the reaction for forming carbon-carbon bonds is an aldol condensation.

10. The method according to claim 6, wherein the reaction for forming carbon-carbon bonds is a Michael addition.

11. The method according to claim 6, wherein the reaction for forming carbon-carbon bonds is a Mannich reaction.

12. The method according to claim 6, wherein the reaction for forming carbon-carbon bonds is a Henry reaction.

13. The method according to claim 6, wherein n is 0 and the α-amino acid is proline.

14. The method according to claim 6, wherein n is 9 and the α-amino acid is proline.

15. The method according to claim 10, wherein X is 1 and Y is 3.

16. The method according to claim 11, wherein X is 1 and Y is 6.

* * * * *